US00RE43116E

(19) United States
(12) Reissued Patent
Johnson

(10) Patent Number: US RE43,116 E
(45) Date of Reissued Patent: Jan. 17, 2012

(54) PACKABLE CERAMIC BEADS FOR BONE REPAIR

(75) Inventor: James R. Johnson, Stillwater, MN (US)

(73) Assignee: Phillips Plastic Corporation, Phillips, WI (US)

(21) Appl. No.: 11/263,675

(22) Filed: Oct. 31, 2005

Related U.S. Patent Documents

Reissue of:
(64) Patent No.: 6,869,445
Issued: Mar. 22, 2005
Appl. No.: 09/564,431
Filed: May 4, 2000

(51) Int. Cl.
*A61F 2/44* (2006.01)
*A61F 2/28* (2006.01)
*B29C 67/24* (2006.01)

(52) U.S. Cl. ..... 623/17.11; 623/16.11; 264/123

(58) Field of Classification Search ..... 623/17.16, 623/16.11, 17.11; 521/56, 57; 523/113; 427/2.26; 424/423; 264/123
See application file for complete search history.

(56) References Cited

U.S. PATENT DOCUMENTS

| | | | |
|---|---|---|---|
| 2,093,454 | A | 9/1937 | Kistler |
| 3,508,941 | A | 4/1970 | Johnson |
| 4,090,022 | A | 5/1978 | Tsao et al. |
| 4,246,211 | A | 1/1981 | Kuhnel |
| 4,246,221 | A | 1/1981 | McCorsley, III |
| 4,341,663 | A | 7/1982 | Derleth et al. |
| 4,416,698 | A | 11/1983 | McCorsley, III |
| 4,430,760 | A | 2/1984 | Smestad |
| 4,452,905 | A | 6/1984 | Drinkuth |
| 4,563,489 | A | 1/1986 | Urist |
| 4,596,574 | A | 6/1986 | Urist |
| 4,610,832 | A | 9/1986 | Brcokmeyer |
| 4,755,184 | A | 7/1988 | Silverberg |
| 4,839,215 | A | 6/1989 | Starling et al. |
| 4,863,472 | A | 9/1989 | Tomala et al. |
| 5,015,255 | A | 5/1991 | Kuslich |

(Continued)

FOREIGN PATENT DOCUMENTS

| | | |
|---|---|---|
| CA | 791040 | 7/1968 |

(Continued)

OTHER PUBLICATIONS

Harmon et al., "Thermodynamic and IR study of the hydrates of N-methylmorpholine oxide and quinucdlidine oxide. Effect of hydrate stoichiometry on strength of H-O-H . . . O-N hydrogen bonds; implications for the dissolution of cellulose in amine oxide solvents." *Journal of Molecular Structure,* Eleseview Science Publishers 1992.

(Continued)

*Primary Examiner* — Bruce E Snow
(74) *Attorney, Agent, or Firm* — Fredrikson & Byron, P.A.

(57) ABSTRACT

Adherent packed beds of ceramic beads, each comprising a ceramic body coated with a biodegradable polymer, and fabric bags containing such beads in a packed, self-supporting configuration. The polymeric coating provides some resilience to a packed bed of the ceramic beads, and prevents the beads from moving with respect to each other when placed under stress, leading to reduced breakage. The ceramic beads desirably are osteoconductive, and preferably are formed of a ceramic material that is resorbed during bone growth, such as hydroxyapatite, tricalcium phosphate, or mixtures of these materials. The beads may contain, either internally or on their surfaces or both, a bone morphogenic protein, and the latter may also be included in the biodegradable polymer coatings on the beads.

37 Claims, 1 Drawing Sheet

U.S. PATENT DOCUMENTS

| | | | | | |
|---|---|---|---|---|---|
| 5,055,429 | A | | 10/1991 | James et al. | |
| 5,252,284 | A | | 10/1993 | Jurovic et al. | |
| 5,366,756 | A | * | 11/1994 | Chesterfield et al. | 427/2.26 |
| 5,540,874 | A | | 7/1996 | Yamada et al. | |
| 5,549,679 | A | | 8/1996 | Kuslich | |
| 5,571,189 | A | | 11/1996 | Kuslich | |
| 5,922,025 | A | * | 7/1999 | Hubbard | 424/423 |
| 5,977,204 | A | * | 11/1999 | Boyan et al. | 523/113 |
| 5,997,603 | A | | 12/1999 | Noro et al. | |
| 6,165,486 | A | * | 12/2000 | Marra et al. | 424/423 |

FOREIGN PATENT DOCUMENTS

| | | |
|---|---|---|
| DE | 198 38 263 | 3/1999 |
| EP | 0271236 | 11/1987 |
| GB | 2259252 A | 10/1993 |
| JP | 60 215516 | 10/1985 |

OTHER PUBLICATIONS

Maruno et al., "Micro-observation and characterization of bonding between bone and HA-glass-titanium functionally gradient composite," *Biomaterials* Mar. 1991, vol. 12.

Kim, Seong Su, et al. "Ultrastable Mesostructured Silica Vesicles," *Science* Nov. 13, 1998 pp. 1302-1305.

Takao, Yasumasa, et al. "Preparation of a multilayer and a compositional gradient layer composite by the aerosol filtration method," J. Mater. Res., vol. 9, No. 8, Aug. 1994 pp. 2128-2132.

Adoba, A.E., et al. Study of the Mechanical Properties and Bioactivity of Functionally Graded Titanium Matrix Composites Reinforced with Bioactive Particles, Proceeding: Eleventh International Conference on Composite Materials, Australian Composite Structrures Society Woodhead Publishing Limited, Queensland, Australia, Jul. 14-18, 1997. pp. I-496-I-508.

Stack, M. M. and Pena, D., "Surface Engineering of Composite and Graded Coatings for Resistance to Solid Particle Erosion at Elevated Temperatures," Advances in Surface Engineering, Volum III: Engineering Application pp. 260-276.

Pratapa, S., et al., "Infiltration-processed, functionally graded aluminum titanate/zirconia-alumina composite; Part I Microstructural characterization and physical properties," *Journal of Materials Science,* Perth, Australia, pp. 3037-3045.

Pratapa, S., et al., "Infiltration-processed, functionally graded aluminum titanate/zirconia-alumina composite; Part II Mechanical properties," *Journal of Materials Science,* Perth, Australia, pp. 3047-3053.

Database WPI, Section Ch, Week 199228, Derwent Publciations, London, GB Class A96, AN 1992-231254 Xp002177315 & JP 04 156840 (Sumitomo Cement Co.) May 29, 1992, Abstract.

* cited by examiner

PACKABLE CERAMIC BEADS FOR BONE REPAIR

Matter enclosed in heavy brackets [ ] appears in the original patent but forms no part of this reissue specification; matter printed in italics indicates the additions made by reissue.

FIELD OF THE INVENTION

The invention relates to coated ceramic beads that are packable to form a bone substitute material.

BACKGROUND OF THE INVENTION

Proper bone healing and subsequent favorable bone remodeling are dependent on maintaining stability between bone fragments, and on maintaining physiologic strain levels. Successful bone graft procedures commonly require an osteoconductive matrix providing a scaffold for bone in-growth, osteoinductive factors providing chemical agents that induce bone regeneration and repair, osteogenic cells providing the basic building blocks for bone regeneration by their ability to differentiate into osteoblasts and osteoclasts, and a substantially stable implant site. Current bone graft materials include autografts, allografts, and a variety of artificial or synthetic bone substitute materials.

For structural bone repair materials to be conveniently used, they must be capable of being formed into complex shapes that are designed to fit the contours of the repair site. Accurately contoured grafts enhance the integration of the natural bone and provide better load carrying capability. Intimate, load-carrying contact often is required between the natural bone and the bone substitute material to promote bone remodeling and regeneration leading to incorporation of the graft by host bone. A general overview of orthopedic implantable materials is given in Damien, Christopher J., and Parsons, Russell J., "Bone Graft and Bone Graft Substitutes: A Review of Current Technology and Applications", Journal of Applied Bio Materials, Volume 2, pp. 187-208 (1991).

Bone substitute materials have found particular use in the repair of lower back disc deterioration, and a method and a device for such repair is disclosed in Kuslich, U.S. Pat. Nos. 5,549,679 and 5,571,189, respectively. These patents describe a surgical operation in which a bore is drilled laterally into a deteriorated disc body, the bore being enlarged into the bony vertebral bodies above and below the disc to form an enlarged, desirably rounded cavity. The physician then inserts a flexible fabric bag into the cavity and fills the bag with a particulate bone substitute material. The preferred fill material is identified as finely chopped cortical or cancellous bone chips for fusion, hydroxyapatite or similar biocompatible materials, or connective tissue when a fibrous union is desired. Once the bag is packed full, its mouth is closed off, and surgical access to the site is repaired in the usual fashion.

In connection with the procedure described in the above patents, experiments have been performed to replace the cortical or cancellous bone chips with other particulate materials, including particularly ceramic beads. The beads may be formed of zirconia, alumina, hydroxyapatite, or other ceramic material, and may be generally cubic in shape with the sharp edges of the cubes rounded off. As ceramic beads of this type are packed tightly within a fabric bag, the beads may grate against each other, generating fine particulates, as they seek relatively stable positions with respect to each other. Moreover, the beads themselves may actually break when subjected to packing forces. Even when packed tightly, the beads still may move slightly with respect to one another in response to shifting loads until bone in-growth stabilizes their positions. It is desirable to inhibit such movement also, inasmuch as such movement may create local configurations of high stress, leading to bead fracture.

It would be desirable to provide ceramic beads that are resistant to relative movement and fracture when packed together, as, for example, in a fabric bag according to the teachings of the above patents, and which moreover may include osteoconductive and osteoinductive materials such as bone morphogenic protein to foster bone ingrowth.

SUMMARY OF THE INVENTION

We have found that ceramic beads each comprising a ceramic body coated with a biodegradable polymer can be particularly useful when employed in the surgery referred to above. The polymeric coating provides some resilience to a packed bed of the ceramic beads, and also helps to render the beads less friable when moved over m one another under stress. The ceramic beads desirably are osteoconductive, and preferably are formed of a ceramic material that is resorbed during bone growth, such as hydroxyapatite, tricalcium phosphate, or mixtures of these materials. The beads may contain, either internally or on their surfaces or both, a bone morphogenic protein, and the latter may also be included in the biodegradable polymer coatings on the beads.

Structurally, the beads may be solid and dense, or may be porous. Solid, dense beads provide a higher modulus of elasticity and exhibit greater strength than do porous beads. However, the lower modulus of elasticity of porous beads more closely approaches the modulus of elasticity of natural bone. Porous beads useful in the present invention may have a continuous, strong supportive framework of struts providing a plurality of interconnecting interstices forming pores that extend through their volumes and open onto their surfaces. Bone morphogenic protein may be received in and carried by the pores, so as to be available for encouraging bone growth.

Thus, in one embodiment, the invention provides ceramic beads that are useful, when packed or clumped together, as a bone substitute material. The beads each comprise a ceramic body having an outer surface defining a shape having a bulk volume. The outer surfaces of the beads bear a substantially continuous coating of a biodegradable polymer, the coating providing a surface enabling the beads to pack together into a coherent, load-supporting mass when subjected to compressive forces to avoid bead breakage due to rubbing together of adjacent beads, but enabling the beads to flow freely past each other when uncompressed. The polymeric coatings provide the packed beads with a measure of resiliency to harmlessly absorb impact forces that otherwise might lead to brittle failure of beads.

In another embodiment, the invention relates to an article useful for replacing or stabilizing bone. The article comprises a fabric bag formed of a fabric having openings sized to enable bone growth therethrough. Packed within the bag is a plurality of in ceramic beads of the type described above. At points of contact between the beads, the biodegradable polymer coatings on the outer surfaces of the beads restrain the beads from sliding past one another when in their packed orientation in the bag. The coatings also provide a thin, resilient cover to lessen the effects of sudden forces such as compression impact forces. The bag packed with polymer-coated ceramic beads, as thus described, provides a stable implant structure useful in spinal and other orthopedic procedures.

As mentioned earlier, the beads may, if desired, have a continuous, strong supportive framework of struts providing a plurality of interconnecting interstices that define interconnecting openings or pores that extend throughout the volume and opening through the ceramic surface of the beads and preferably also opening through the biodegradable polymer coating.

DETAILED DESCRIPTION OF THE PREFERRED EMBODIMENT

Figure 1:
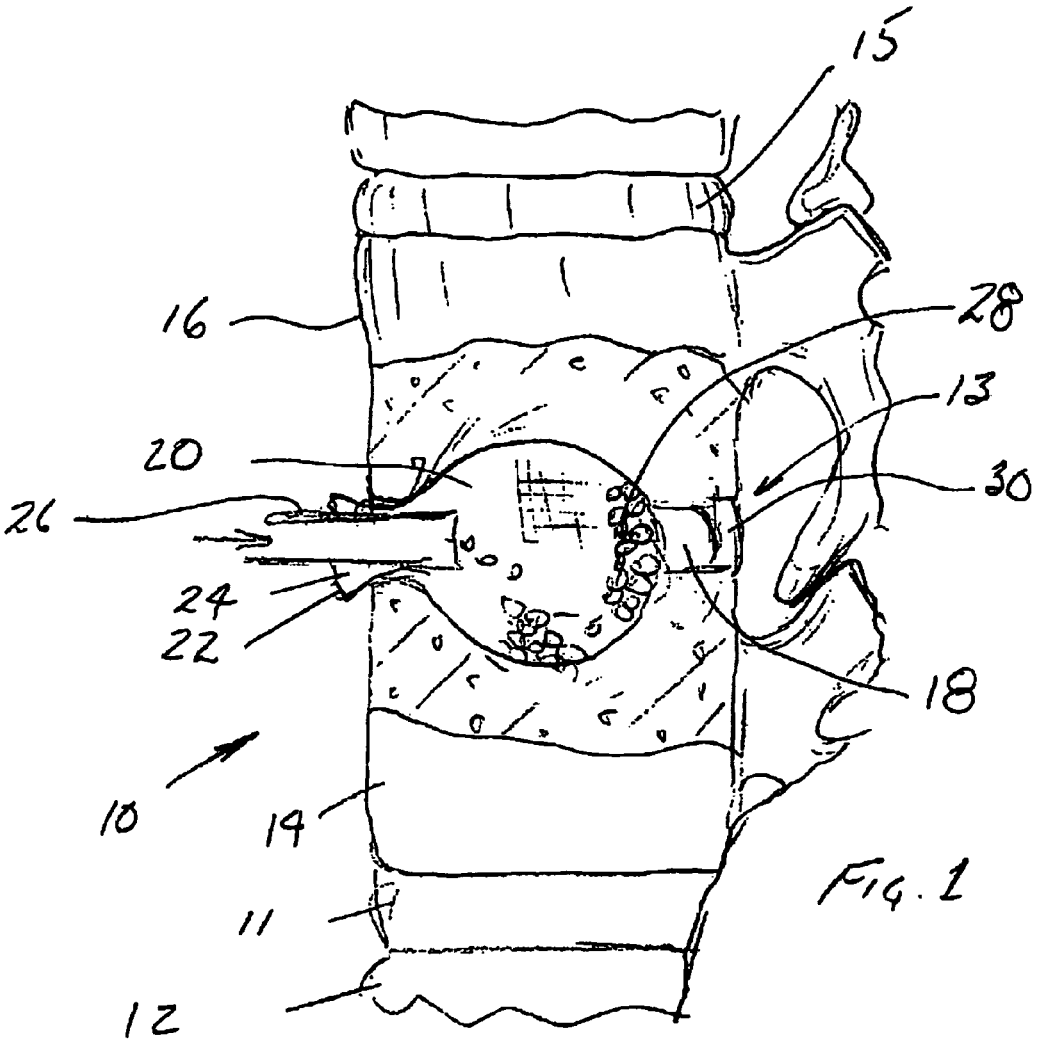
FIG. 1 is a broken-away diagrammatic view, partially in cross section, showing a step in the method of the invention for repairing a spinal injury.

The beads useful in the invention may be of substantially any biocompatible ceramic material, but preferably are of those ceramic materials that are osteoconductive, and especially those that can be resorbed in the process of bone ingrowth. Appropriate ceramic materials include hydroxyapatite, tricalcium phosphate, and mixtures thereof. As desired, the beads also may include one or more non resorbable ceramic materials such as zirconia or alumina. When the ceramic is resorbable, as when a mixture of hydroxyapatite and tricalcium phosphate is employed, the resulting structure upon healing will be bone formed through bone ingrowth. On the other hand, when a portion of the ceramic is of a non resorbable material such as zirconia, there remains in the supporting structure a zirconia network, and this may add desired rigidity to the bone structure.

The ceramic beads themselves may be solid, dense structures or may exhibit varying degrees of porosity. In one embodiment, the beads to which a coating may be applied as described below have pores extending throughout their bulk volume. Desirably, each bead comprises a ceramic body having an outer surface defining a shape having a bulk volume, and having a continuous strong supportive framework of struts providing a plurality of interconnecting interstices or pores. The beads of the invention preferably are spheroidal in shape, and although different sizes of beads can be mixed together and employed in the invention, it is desired that the beads be of a substantially uniform size to provide proper packing and to allow for continuous openings to be maintained between beads when they are packed together. That is, it is preferred to avoid the use of mixtures of beads of different sizes in which smaller beads may plug or greatly restrict the openings between larger beads.

When porous beads are employed, the internal, interconnecting interstices of each bead define openings that extend throughout the volume of the bead and that open through the surface of the beads, the pores thus being "accessible" from the beads' exterior. Beads may be manufactured to have pores of various diameters. Preferably, the beads are made with pores in the range of about 0.3 to about 50 microns.

Porous ceramic beads may be made by a process in which a viscous sol of a polymer such as cellulose and a primary solvent such as N-methyl-morpholine-N-oxide ("NMMO"), when contacted with a secondary solvent such as water or alcohols with which the primary solvent is miscible but in which the polymer is not soluble, will coagulate as the primary solvent is extracted from the sol, leaving behind an open polymeric structure. Reference is made to U.S. Pat. No. 4,246,221 (McCorsley), U.S. Pat. No. 4,416,698 (McCorsley), U.S. Pat. No. 5,252,284 (Jurkovic, et al.) and U.S. Pat. No. 5,540,874 (Yamada, et al.). See also, U.S. Pat. No. 3,508,941 (Johnson).

As described in co-owned U.S. patent application Ser. No. 09/286,919, filed Apr. 6, 1999 and entitled "Sinterable Structures and Method", sinterable ceramic materials such as hydroxyapatite, tricalcium phosphate, zirconia, alumina, etc. can be mixed with the viscous sol of the polymer. Thereafter, the mixture can be coagulated to form a gel by contact with a secondary liquid in which the polymer is not soluble and which extracts and replaces the primary solvent, leaving behind a fine, open polymeric network having the sinterable powder arranged in it. The material can be appropriately shaped into fibers, sheets, tubes, etc., either in the form of the viscous sol (e.g., by extrusion), or by shaping the resulting gel.

Of particular utility here is a process in which the viscous sol containing the ceramic particulates is flowed, drop-by-drop, into a non-solvent for the sol, such as a 50/50 percent by volume water/NMMO blend. The resulting spheroidal particles may be collected, dried on a screen in a drying oven, and thereafter may be heated slowly to sintering temperatures. During the temperature escalation, the organic sol material is removed by pyrolysis, leaving behind it a network of the sinterable ceramic particles in contact with one another. Finally, as the material is raised to sintering temperatures, the ceramic particles, still in a configuration mandated by the configuration of the gel, sinter to form strong, spheroidal, porous, self supporting ceramic beads. The latter, having pores ranging in diameter from about 0.3 to about 50 microns in size and extending completely through the volume of the beads, is substantially different from the semi-porous product resulting from the simple sintering of ceramic powders compressed into shapes. In the latter case, the pores or openings that are initially present between particles become smaller and closed off as the particles coalesce into one another sufficiently to form self supporting ceramic shapes, the pores eventually becoming largely sealed off as the density of the material increases.

In any event, porous ceramic beads useful in the invention may be made by first preparing a viscous mixture comprising a sinterable, ceramic powder or mixture of powders, of such ceramics as hydroxyapatite, tricalcium phosphate, zirconia, alumina, or the like, in a sol of a polymer such as cellulose in a primary solvent such as NMMO, replacing the primary solvent with a secondary liquid in which the polymer is insoluble (such as a water/NMMO mixture) to produce a gel comprising an open polymeric network having the sinterable powder arranged therein, removing the secondary liquid from the gel, and raising the product to sintering temperatures to remove the polymeric structure and to form the desired open, porous ceramic structure. As mentioned earlier, it is desired that the viscous mixture containing the ceramic powder and a primary solvent be added as droplets to the secondary solvent so as to produce a spheroidal particle.

The porous interiors of the ceramic particles described above may be filled at least partially with a bone morphogenic protein to induce formation of new bone. Bone morphogenic protein is readily available from commercial sources, and a particular bone morphogenic protein, BMP-7, sold as OP-1 by Stryker Biotech, a division of Stryker Corp., is appropriate for this purpose. Bone morphogenic protein may be contained throughout the pore volume of the bead, and in this embodiment it is important that the pores of the bead extend completely through the bead volume, being accessible and open at the surface of the bead.

The use of bone morphogenic protein in connection with ceramic materials has been described in U.S. Pat. No. 4,596,574 (Urist), the ceramic materials there being formed through a powder sintering technique. The teachings of the Urist '574 patent are incorporated herein by reference. In connection with beads of the invention, bone morphogenic protein, in the form of a powdery solid, may be combined with the beads either before or after applying to them the biodegradable polymer coating, and through impact/agitation (as by ball milling), the powder is incorporated onto the coated or uncoated bead surfaces or, if applied prior to the polymer coating, at least partially within the pores of the beads. It is contemplated that bone morphogenic protein powder may applied to the beads using electrostatic attraction techniques in which the beads and the powder particles are given opposite charges.

Bone morphogenic protein may be incorporated into the beads by various techniques using liquid or gel-like vehicles. For example, a bone morphogenic protein powder such as BMP-7 may be dissolved in a saline solution, and porous beads may be suitably contacted by the solution, e.g., by immersion, to cause the solution to enter the pores. Penetration of the solution into the pores may be facilitated by drawing a vacuum to cause the beads to outgas, the solution replacing the escaped gas (air, for example) within the beads. The beads may then be dried to leave behind in the pores a residuum of the protein. If desired, the protein solution may remain in the beads as they are inserted in the bag, or the solution may be added to the beads as they are contained in the bag, as through the use of an appropriate syringe. In general, the pores of the particles are so small as to readily retain the solution within the pores by capillary action. If the retention of the solution in the beads by capillary action is not sufficient, a biologically acceptable thickening agent such as collagen, chitosan, or a polymer such as poly (vinyl alcohol) or methyl cellulose may be included in the solution to increase its viscosity. The concentration of bone morphogenic protein in the pores can be increased by repeatedly contacting the beads with a solution of the bone morphogenic protein and then drying to remove solvent.

The ceramic surfaces of the beads bear a coating of a biodegradable polymeric material. The preferred biodegradable polymers are poly (lactic acid) ("PLA") and poly (glycolic acid) ("PGA"). Preferably a lactic acid—glycolic acid copolymer made from approximately equimolar quantities of lactic acid and glycolic acid monomers is used, the rate of biodegradation being a function of the ratio of these monomers. The polymers themselves may be deposited on the surface of the ceramic beads by any appropriate means. In a preferred coating method, the beads may be suspended in an upward flow of gas to form a fluidized bed. A fine spray of a solution of biodegradable polymer is introduced to the fluidized bed, fine droplets of the solution being received on the ceramic surfaces of the beads to coat the beads and the solvent being evaporated from the beads by continued flow of the gas.

Alternatively, the polymers may be applied from solution, for example, by preparing a solution of a biodegradable polymer or polymers in an appropriate solvent such as methylene chloride. The beads are withdrawn from the polymer solution after a few seconds. When porous beads are employed, the time that the beads remain in the solution is related to the penetration of the polymer solution into the pores of the beads. After removal from the solution, the beads may be placed on a screen or other suitable support enabling the beads to remain separate from one another. Use of a screen made of a wire or a polymer meshwork enables the beads to be supported in separate mesh openings to prevent the beads from sticking together. The coated beads may be air dried with moisture-free air, and are stored in a desiccator.

The coating that is applied to the beads is substantially continuous. Complete coverage, of course, is not required. In the case of porous beads, some of the biodegradable polymer solution may be received within the pores, and the pores themselves open through the coating. The coating on the exterior of the beads is substantially complete in any event, and may range in thickness from about 50 to about 200 nm based upon the weight gain of the beads resulting from the coating process and upon SEM estimates. Thus, in the case of porous beads, the thickness of the coating is preferably less than the diameter of the pores and most preferably at least an order of magnitude less than the pore diameter.

If desired, bone morphogenic protein may be included in the polymer coating to encourage bone in-growth. This can be accomplished by incorporating the bone morphogenic protein in a solution of the polymeric material utilizing a solvent system that accommodates both the bone morphogenic protein and the biodegradable polymer, such as poly (glycolic acid). As noted above, the bone morphogenic protein also could be incorporated in the coating by simply applying it as a dry powder to the coated surface of the beads, and such application to the coating before the latter has completely dried may prove advantageous. Impact/agitation, as by ball milling the beads with added powder, also may serve to incorporate the protein powder at least slightly into the coating so that little of the powder is lost as the beads are flowed into a bag.

The biodegradable polymer-coated surfaces of the beads, when dry, permit the beads to flow past each other readily as they are poured from one container to another, for example. The coating protects the beads from breakage and fragmentation during flow as in the filling and packing process. If the beads are not placed under pressure by compacting them together, they continue to flow readily. However, once the beads are packed together and subjected to a compressive force, as occurs within the fabric bag used in the spinal surgery referred to above, the polymer coating on the beads tends to cause the beads to stick together. It is believed that the polymer coatings merge at points of contact of the beads, thus enabling the beads to clump or pack together into a coherent mass.

Through the use of spheroidal beads, preferably of a fairly uniform diameter, a tortuous pathway between the packed beads is thus obtained. Of importance, the coatings enable the beads to pour easily and thus to arrange themselves into a closely packed mass on the one hand, but once the beads are packed tightly and thus are under some compression, the coating serves to restrain the beads from rubbing against one another, and thus minimizes bead breakage or powdering. Moreover, the coated beads, when packed together, tend to stick together, affording a degree of resilience to the packed mass of beads.

The beads themselves preferably have sizes ranging from about 1 to about 5 mm, and, as noted, are preferably generally spheroidal. Also, it is desired that the beads for use in a bag procedure, as will now be described, be of a uniform size to facilitate packing and also to maintain an open pathway between beads.

The use of beads of the invention in a surgical procedure is exemplified and illustrated in FIG. 1. FIG. 1 shows a portion of a spinal column designated generally as 10, the spinal column being made up of alternating vertebrae 12, 14, 16 and discs 11, 13, 15. We will assume for purposes of illustration that disc 13 has suffered degeneration.

In accordance with the procedures set out in Kuslich, U.S. Pat. No. 5,549,679, a bore 18 is formed through the annulus fibrosis 30 or outer wall of the disc, the bore extending between the vertebral bodies 14 and 16. The depth of the bore is nearly through the width of the disc, but terminates short of the far wall or annulus fibrosis 30 of the disc. A bore diameter of about 10 mm is appropriate, and the depth of the bore may be on the order of about 25 mm, for example, when the disc being operated upon is between the fourth and fifth lumbar vertebrae in the spine of a typical adult human male. The diameter of the chamber is then increased by cutting a shallow cavity into the vertebrae immediately above and below the disc, the chamber being formed as shown in FIG. 1 so as to be bulbous or generally spheroidal in shape. Enlargement of the cavity without increasing the size of the entry bore is desirable for containment and stability of the implant. An expanding cutting tool of the type shown in Kuslich, U.S. Pat. No. 5,062,845, may be employed, the teachings of which are incorporated herein by reference. Enlargement of the cavity, as outlined in Kuslich '679, is also a necessary step for removing degenerated disc material and exposing bone in the vertebral bodies, to increase the likelihood of successful graft incorporation. It will be understood that the surgery thus far described can be accomplished from an anterior or posterior surgical approach.

Into the enlarged chamber 20 thus prepared is placed a porous fabric bag 22 having a shape, when inflated, that is generally the same as the shape of the chamber 20 but that is slightly larger than the chamber. Into the upwardly open mouth 24 of the bag is placed an introducer tube 26, and through this tube the beads of the invention, designated generally as 28, are introduced into the bag. Continued addition of beads causes the bag to expand into intimate contact with the walls of the chamber 20, the beads flowing past one another into a closely packed configuration. As the bag expands, accordingly, its outer surfaces abut against the opposing surfaces of the vertebrae 14, 16 that are below and above the disc 13, respectively. Continued expansion of the bag causes the vertebrae to separate slightly and to thus tighten the annulus fibrosis 30 of the disc 13. The beads 28, as they enter the bag 22, flow readily past one another to completely occupy the interior of the bag. Blood, marrow, or finely chopped pieces of bone, separately or in combination, also may be added to the bag during the filling process if desired. This can help to provide autogenous osteoconductive and osteoinductive materials to the implant site. Once the bag has been completely filled and packed with beads, the mouth 24 of the bag is sealed, as with a drawstring (not shown) or the like.

The fabric bag may be made of polyester or other appropriate biocompatible material. "Fabric" will be understood to mean both a woven structure and also a film or sheet-like structure with perforations formed through its walls. The fabric must be sufficiently flexible to enable it to be collapsed and inserted into the cavity formed between adjacent vertebrae, but must be strong enough to avoid tearing or ripping when it is filled with the beads of the invention.

The beads, as thus packed within the bag, form a stable, non-moving mass that, in the preferred embodiment utilizing porous beads, exhibits porosity on two levels. First, the mass of generally spheroidal beads that are closely packed together provides a series of voids between the beads and enables body fluids and eventually bone to penetrate completely through the bag contents. Second, the beads themselves, when porous, may advantageously carry bone morphogenic protein or other bone growth materials and may thus supply such bone growth materials to the site of desired bone growth. Thus, the beads as loaded and packed into the chamber 20 form a solid, coherent body, the biodegradable polymer coatings at points of contact between the beads serving to restrain the beads from moving past one another under a shifting or varying load and in this manner restraining breakage or powdering of the beads.

In the following, non-limiting examples, coated ceramic particles were packed into a polyester bag and subjected to repeated mechanical loading. For each Example, both coated and uncoated (control) particles were thus tested.

EXAMPLE 1

Sintered ceramic cubes of hydroxyapatite, about 2 mm in size that had been partially rounded by treatment in a vibratory mill were supplied by Ceramed Co. The density of the cubes was greater than 98% of theoretical. These were coated by dipping into a solution of 0.75 grams of a copolymer made of equal amounts of PGA and PLA (Alkermes Corp) dissolved in 10 cc. of methylene chloride. The coated cubes were tumble-dried on a metal screen in dry air for 10 minutes and stored in a dessicator filled with argon. The coated cubes did not adhere to one another. The polymer is essentially solid but resilient. The cubes were later inserted into a polyester fabric bag—about 1 inch in diameter using a mechanical tool that packed them tightly via impact and vibrational loading. The particle-filled bag was subjected to intense mechanical loading and twisting up to one million cycles using an Enduratec biaxial testing machine that applies both compressive and torsional loading to the specimens.

EXAMPLE 2

Example 1 is repeated, except that the ceramic cubes are made of zirconia supplied by Coors Corp.

EXAMPLE 3

Example 2 is repeated, except that the solution contains 1.5 grams of the PGA-PLA copolymer in 10 cc of methylene chloride.

EXAMPLE 4

Example 2 is repeated, except that the ceramic cubes are made from porcelain supplied by Continental Clay Co., Minneapolis, Minn.

EXAMPLE 5

In a 150 mL beaker is placed 70 cc of N-methyl morpholine oxide/water in a 50:50 mixture by weight. Using a stir bar on a magnetic stirring heating mantle, the mixture is stirred at a medium rate while 2.6 g of the powdered cellulose (Aldrich Chemical Company) with an average particle size of 20 μm is added. The mix is then heated and stirred to form a smooth, clear, viscous, orange sol. While this sol is still hot, 15.0 g of a powder containing by weight 85% of hydroxyapatite ("HA") and 15% of tricalcium phosphate ("TCP") is added and is stirred into the viscous sol until an even suspension forms, identifiable by the lack of hydroxyapatite clumps and by an overall smooth, milky white appearance.

The resulting material is transferred to a syringe and the material is added drop by drop to a water bath. Generally spheroidal particles are formed in the water, and the water replaces the N-methyl morpholine oxide. The resulting spherical particles are dried at 50° C. on a wire mesh, and then removed from the wire mesh support and heated to 1200° C. to pyrolize the cellulose and to sinter the hydroxyapatite/TCP ceramic. The resulting product is a strong, microporous ceramic spheroidal bead having a diameter of about 2 mm. The particles are then coated and tested as in Example 1.

EXAMPLE 6

Example 5 is repeated, except that the composition of the ceramic spheres by weight is 65% of HA and 35% of TCP.

EXAMPLE 7

Spheroidal particles made as in example 6 were immersed in a water saline solution containing a red dye. The spheres are tested to reveal the penetration of the dye and are weighed before and after to determine the amount of solution absorbed. In these open porous spheres (about 40% porosity) essentially all of the pores were filled with solution.

EXAMPLE 8

To provide visual evidence of the degree of adherence of powdered bone morphogenic protein to the surface of particles, spheroidal particles made as in Example 6 were tumbled in a black iron oxide powder for 30 seconds to coat the powder onto the PGA-PLA coating on the spheres. (10 grams powder to 2 grams spheres). Methylene chloride (1% by weight) was mixed with the black powder prior to tumbling in a ball mill. Nearly all of the black powder adhered to the ceramic sphere.

Results

It is believed to be of great importance to prevent the particulate materials during the bone healing process from moving with respect to each other when placed under physical loads. Such stability is important as the bone restoration process proceeds until ingrown natural bone takes over the stabilizing function. Bead breakage can result in loss of stability of the packed bed; the resulting chips and dust can fill voids that are necessary for ingrowing bone and it is believed that finely powdered HA can interfere with osteogenesis.

In each of the above Examples, the bags after repeated torsion and compression to loading were examined with respect to bead adherence and with respect to bead breakage and the unwanted formation of powdered bead fragments.

Our examination of the coated beads of each Example showed the beads to remain adhered together, to remove them from the bag, one had to pry them loose. In contrast, when uncoated beads were used, no adherence was observed; and the beads were loose in the bag.

Initial tests with the porcelain particles showed about two fold decrease in breakage (measured by the percent of beads that were broken), coated over uncoated. The HA and zirconia rounded cubes showed a 2 to 4 fold decrease in breakage, coated over uncoated. The porous spheres of HA-TCP compositions have shown up to a nine fold decrease in breakage, coated over uncoated, with less than 1% of the spheres showing any damage.

While several forms of the invention have been shown and described, other forms will be apparent to those skilled in the art. The embodiments shown on the drawings and described above are merely for illustrative purposes and are not intended to limit the scope of the invention, which is defined by the claims which follow.

What is claimed is:

1. An article useful for replacing bone in orthopedic procedures, the article comprising a fabric bag formed of a fabric having openings sized to enable bone growth therethrough, and a plurality of ceramic beads packed within said bag, said beads including beads each comprising a single ceramic body having an outer surface defining a shape having a bulk volume, the outer surfaces of said beads bearing a substantially continuous coating of a biodegradable polymer, said coating enabling said beads to form a coherent, load-supporting mass when subjected to compressive forces to restrain bead breakage due to rubbing together of adjacent beads.

2. The article of claim 1 wherein said beads have a continuous strong supportive framework of struts providing a plurality of interconnecting interstices defining interconnecting openings extending throughout said volume and opening through the ceramic surface of the beads.

3. The article of claim 2 wherein said interconnected openings open through said biodegradable polymer coating.

4. The article of claim 1 wherein said beads are packed together to provide a plurality of openings between said beads and wherein said coatings merge at points of contact between beads.

5. The article of claim 1 wherein the ceramic body is osteoconductive.

6. The article of claim 1 wherein the ceramic body comprises hydroxyapatite, tricalcium phosphate, or a mixture thereof.

7. The article of claim 1 wherein the ceramic body additionally comprises a non-resorbable ceramic.

8. The article of claim 2 including bone morphogenic protein carried within said interconnected openings.

9. The article of claim 1 including bone morphogenic protein carried within said coating.

10. The article of any one of claims 1-9 wherein said ceramic body shape is generally spheroidal and wherein said beads are substantially uniform in size.

11. An article useful for replacing bone in orthopedic procedures, the article comprising a fabric bag formed of a fabric having openings sized to enable bone growth therethrough, said bag having packed therein a plurality of ceramic beads each comprising a ceramic body having an outer surface defining a shape having a bulk volume, the outer surfaces of said beads bearing a substantially continuous coating of a biodegradable polymer and said beads having continuous openings between them, said coating enabling said beads, when subjected to compressive forces, to form a coherent, load-supporting mass when said beads are subjected to compressive forces to restrain bead breakage due to rubbing together of adjacent beads.

12. The article of claim 11 wherein said ceramic bodies are generally spheroidal.

13. The article of claim 12 wherein said ceramic bodies are substantially uniform in size.

14. An article useful for replacing bone in orthopedic procedures, the article comprising a fabric bag formed of a fabric having openings sized to enable bone growth therethrough, and a plurality of ceramic beads packed within said bag, said beads including beads each comprising a single ceramic body having an outer surface defining a shape having a bulk volume, the outer surfaces of said beads bearing a substantially continuous coating of a biodegradable polymer, said coating enabling said beads to form a coherent, load-supporting mass when subjected to compressive forces to restrain bead breakage due to rubbing together of adjacent beads, said packed beads having continuous openings between beads to provide a first level of porosity, and said ceramic bodies comprising a continuous, strong supportive framework of struts providing a plurality of interconnecting interstices that define interconnecting openings that extend throughout the volume and opening through the ceramic surface of the beads to provide a second level of porosity.

*15. A method of forming a bone substitute material comprising the steps of providing beads each formed of a single ceramic body having an outer surface bearing a substantially continuous coating of a biodegradable polymer, and applying to a predetermined volume of the beads a compressive force causing the beads to contact each other and to form a coherent load supporting mass, the coating restraining bead breakage or spalling due to rubbing together of adjacent beads.*

*16. The method of claim 15, wherein the coating is not greater than about one micrometer in thickness.*

*17. The method of claim 15, wherein the coating has a thickness of about one micrometer.*

*18. The method of claim 15, wherein the ceramic body is osteoconductive.*

*19. The method of claim 15, wherein the ceramic body comprises hydroxyapatite, tricalcium phosphate, or a mixture thereof.*

*20. The method of claim 15, further including providing bone morphogenic protein on the surface of the coating.*

*21. The method of claim 15, further including providing bone morphogenic protein within the coating.*

*22. The method of claim 15, each ceramic body comprising a continuous, strong supportive framework of struts providing a plurality of interconnecting interstices that define interconnecting openings, further including providing bone morphogenic protein within the interconnecting openings of the beads.*

*23. The method of claim 15, wherein the polymer is a copolymer made of a poly(lactic acid) and a poly(glycolic acid).*

*24. A method of forming a bone substitute material comprising the steps of providing beads each formed of a single ceramic body having an outer surface bearing a thin, substantially continuous coating of a biodegradable polymer, and applying to a predetermined volume of the beads a compressive force causing the beads to contact each other to form a coherent load supporting mass having continuous openings between the beads, the coating restraining bead breakage or spalling due to rubbing together of adjacent beads and having a thickness of about one micron.*

*25. The method of claim 24, wherein the ceramic body is osteoconductive.*

*26. The method of claim 24, wherein the ceramic body comprises hydroxyapatite, tricalcium phosphate, or a mixture thereof.*

*27. The method of claim 24, further including providing bone morphogenic protein on the surface of the coating.*

*28. The method of claim 24, further including providing bone morphogenic protein within the coating.*

*29. The method of claim 24, each bead having a single ceramic body comprising a continuous, strong supportive framework of struts providing a plurality of interconnecting interstices that define interconnecting openings, further including providing bone morphogenic protein within the interconnecting openings of the beads.*

*30. The method of claim 24, wherein the polymer is a copolymer made of a poly(lactic acid) and a poly(glycolic acid).*

*31. A method of forming a bone substitute material comprising the steps of providing beads each having a single ceramic body comprising a continuous, strong supportive framework of struts providing a plurality of interconnecting interstices that define interconnecting openings and an outer surface bearing a substantially continuous coating of a biodegradable polymer, and applying to a predetermined volume of the beads a compressive force causing the beads to form a coherent load supporting mass, the coating restraining bead breakage or spalling due to rubbing together of adjacent beads and having a thickness of at least an order of magnitude less than the average opening diameter of the interconnecting openings.*

*32. The method of claim 31, wherein the ceramic body is osteoconductive.*

*33. The method of claim 31, wherein the ceramic body comprises hydroxyapatite, tricalcium phosphate, or a mixture thereof.*

*34. The method of claim 31, further including providing bone morphogenic protein on the surface of the coating.*

*35. The method of claim 31, further including providing bone morphogenic protein within the interconnecting openings of the beads.*

*36. The method of claim 31, further including providing bone morphogenic protein within the coating.*

*37. The method of claim 31, wherein the polymer is a copolymer made of a poly(lactic acid) and a poly(glycolic acid).*

* * * * *